(12) United States Patent
Berghofer et al.

(10) Patent No.: US 11,053,193 B2
(45) Date of Patent: *Jul. 6, 2021

(54) MIXED SALTS OF HYDROXYALKANE SULFINIC ACID

(71) Applicant: L. BRÜGGEMANN GMBH & CO. KG, Heilbronn (DE)

(72) Inventors: Josef Berghofer, Tauberbischofsheim (DE); Stefan Mark, Bad Rappenau (DE); Tamara Bittlingmayer, Weinsberg (DE); Jessica Schreiweis, Obrigheim (DE)

(73) Assignee: L. BRÜGGEMANN GMBH & CO. KG, Heilbronn (DE)

( * ) Notice: Subject to any disclaimer, the term of this patent is extended or adjusted under 35 U.S.C. 154(b) by 43 days.

This patent is subject to a terminal disclaimer.

(21) Appl. No.: 16/467,351

(22) PCT Filed: Dec. 12, 2017

(86) PCT No.: PCT/EP2017/082443
§ 371 (c)(1),
(2) Date: Jun. 6, 2019

(87) PCT Pub. No.: WO2018/108922
PCT Pub. Date: Jun. 21, 2018

(65) Prior Publication Data
US 2020/0062701 A1     Feb. 27, 2020

(30) Foreign Application Priority Data
Dec. 13, 2016 (EP) ..................................... 16203719

(51) Int. Cl.
*C07C 313/04* (2006.01)
*C08F 220/12* (2006.01)
(Continued)

(52) U.S. Cl.
CPC .......... *C07C 313/04* (2013.01); *C07C 309/17* (2013.01); *C08F 220/06* (2013.01); *C08F 220/12* (2013.01)

(58) Field of Classification Search
None
See application file for complete search history.

(56) References Cited

U.S. PATENT DOCUMENTS

2002/0042353 A1     4/2002 Berghofer et al.

FOREIGN PATENT DOCUMENTS

EP          1 201 685 A2    5/2002
WO       WO 99/18067 A1    4/1999
(Continued)

OTHER PUBLICATIONS

International Search Report (PCT/ISA/210) issued in PCT/EP2017/082443, dated Apr. 23, 2018.
(Continued)

*Primary Examiner* — Richard A Huhn
(74) *Attorney, Agent, or Firm* — Birch, Stewart, Kolasch & Birch, LLP

(57) ABSTRACT

The preparation and use of mixed salts of hydroxyalkane sulfinic acids and optionally hydroxyalkane sulfonic acids as a reducing agent are disclosed. The reducing power of the salts is significantly higher than the reducing power of the corresponding zinc salt. The storage stability of the salts as solids and as aqueous solution is significantly higher than one of the corresponding sodium salts.

20 Claims, 2 Drawing Sheets

(51) Int. Cl.
*C07C 309/17* (2006.01)
*C08F 220/06* (2006.01)

(56) References Cited

FOREIGN PATENT DOCUMENTS

WO    WO 2013/021234 A1    2/2013
WO    WO 2013/160711 A1    10/2013

OTHER PUBLICATIONS

Written Opinion (PCT/ISA/237) issued in PCT/EP2017/082443, dated Apr. 23, 2018.

MIXED SALTS OF HYDROXYALKANE SULFINIC ACID

The invention relates to mixed salts of hydroxyalkane sulfinic acids and optionally hydroxyalkane sulfonic acids, their preparation and the use of said salts as reducing agent.

BACKGROUND

Formaldehyde sulfoxylates (hydroxymethane sulfinates), in particular sodium formaldehyde sulfoxylate, have proven to be effective and good value reducing agents, in particular in free-radical-initiated emulsion polymerizations. During the reduction process, however, the formaldehyde sulfoxylates eliminate the toxic formaldehyde. Plastics or polymer dispersions which must not contain formaldehyde are polymerized using alternative reducing agents, for example, bisulfites, ascorbic acid, isoascorbic acid or sodium erythrobate. Since the mentioned formaldehyde-free reducing agents are weaker reducing agents, the disadvantage of less complete polymerization compared with formaldehyde sulfoxylates has to be accepted. Moreover, an increased coagulate formation and yellowing is observed with said alternative reducing agents.

The disadvantages of the formaldehyde sulfoxylates have been overcome by the sulfinic acid derivatives which additionally have a carboxylic acid group in the molecule. These derivatives are disclosed in WO 99/18067 and because they have a high reducing power and do not release formaldehyde during or after use they are in wide-spread use as reducing agents, in particular in free-radical-initiated emulsion polymerizations. However, said derivatives are not sufficiently stable in aqueous solution and in particular in acidic media. Consequently, they develop an unpleasant and moreover toxic "sulfur" smell in aqueous or acidic solution along with a significant loss in reducing power. Zinc salts of said sulfinic acids have acceptable stability in aqueous solution but have an unsatisfying reducing power.

SUMMARY OF THE INVENTION

The problem underlying the present invention is therefore to provide a reducing agent which exhibits a high reducing power, in particular, a reducing power that is comparable to that one of said sulfinic acid derivatives, and at the same time a high stability in aqueous solution which is in particular comparable to that one of the zinc salts of the sulfinic acid derivatives.

This problem has been solved by a mixed magnesium-zinc-salt or a mixed aluminium-zinc salt or a mixed calcium-zinc-salt of the sulfinic acid of formula (I)

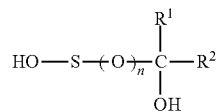

wherein
R$^1$ is H or C$_1$-C$_6$ alkyl,
R$^2$ is COOH, SO$_3$H or CH(OH)S(O)$_n$—OH,
n is 1 and
wherein the acid forms an anion and the counterions are magnesium and zinc ions or aluminium and zinc ions or calcium and zinc ions.

DETAILED DESCRIPTION OF THE INVENTION

Figure 1:
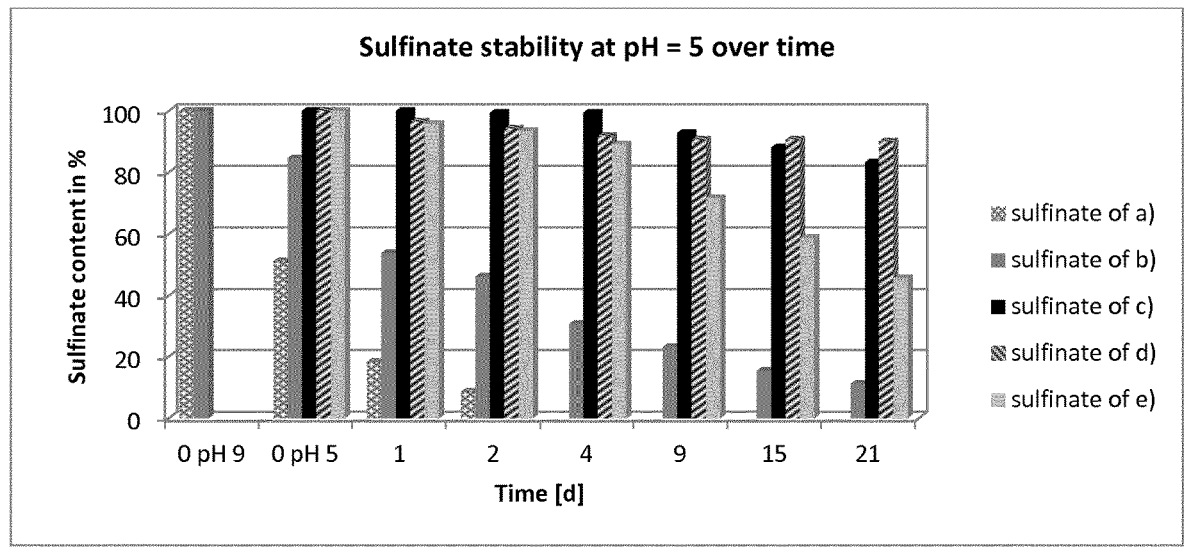
FIG. 1 shows the stability of the salts of the invention over time in an aqueous solution of pH5.

The term "C$_1$-C$_6$ alkyl" as used herein means a straight or branched alkyl group having 1 to 6 carbon atoms. Examples are methyl, ethyl, n-propyl, isopropyl, n-butyl, sec-butyl, isobutyl, tert-butyl, n-pentyl and n-hexyl.

R$^1$ is preferably H. R$^2$ is preferably —COOH. Further preferred are compounds of formula (I) wherein R$^1$ is H and R$^2$ is —COOH.

The mixed salt the invention may additionally contain a mixed magnesium-zinc-salt or a mixed aluminium-zinc-salt or a mixed calcium-zinc-salt of the sulfonic acid of formula (I) wherein n is 2.

The anion is preferably a dianion and has the formula (Iaa), (Ibb) or (Icc)

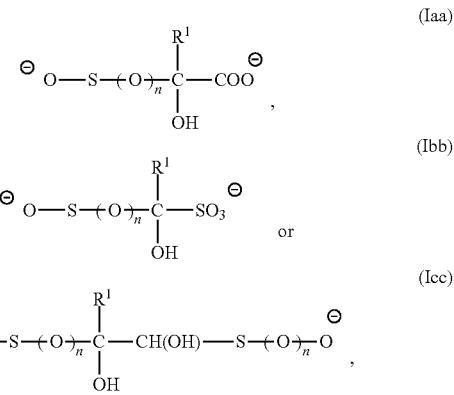

wherein n is as defined above.

In an embodiment, the salt of the invention is a mixed magnesium-zinc-salt of a compound of formula (Ia), (Ib) or (Ic)

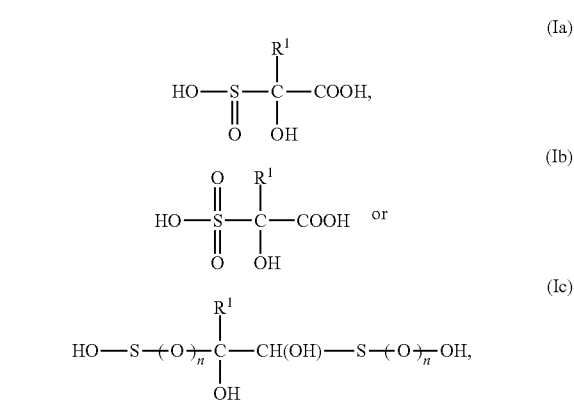

wherein n is independently 1 or 2, but at least one n is 1.

In a further embodiment, the salt of the invention is a mixed aluminium-zinc-salt of a compound of formula (Ia), (Ib) or (Ic).

In a further embodiment, the salt of the invention is a mixed calcium-zinc-salt of a compound of formula (Ia), (Ib) or (Ic).

In a further embodiment, the salt is a magnesium-zinc-salt, wherein the counterions comprise 40 to 60 mole % magnesium ions and 40 to 60 mole % zinc ions and preferably 45 to 55 mole % magnesium ions and 45 to 55 mole % zinc ions.

In a further embodiment, the salt is an aluminium-zinc-salt, wherein the counterions comprise 25 to 60 mole % aluminium ions and 40 to 75 mole % zinc ions and preferably 30 to 50 mole % aluminium ions and 50 to 70 mole % zinc ions.

In a further embodiment, the salt is a calcium-zinc-salt, wherein the counterions comprise 30 to 60 mole % calcium ions and 40 to 70 mole % zinc ions and preferably 35 to 55 mole % calcium ions and 45 to 65 mole % zinc ions.

In a further embodiment, the mixture comprises the sulfinic acid salt and the sulfonic acid salt in a weight ratio of 3:1 to 1:5.

In a further embodiment, the mixture comprises the mixed magnesium-zinc-salt of the sulfinic acid and the mixed magnesium-zinc-salt of the sulfonic acid in a weight ratio of 2:1 to 1:3.

In a further embodiment, the mixture comprises the mixed aluminium-zinc-salt of the sulfinic acid and the mixed aluminium-zinc-salt of the sulfonic acid in a weight ratio of 1:1 to 1:2.

In a further embodiment, the mixture comprises the mixed calcium-zinc-salt of the sulfinic acid and the mixed calcium-zinc-salt of the sulfonic acid in a weight ratio of 3:1 to 1:3.

The salts of the invention may additionally comprise a sulfite salt, in particular magnesium-zinc-sulfite or aluminium-zinc-sulfite. In general, the salt comprises less than 2 wt % of magnesium-zinc-sulfite or aluminium-zinc-sulfite, preferably less than 1 wt % and in particular less than 0.5 wt %. if the salt comprises a sulfite salt then it is present in an amount of at least 0.01 wt %.

A further aspect of the invention is a process for preparing the compounds or compositions of the invention which comprises
a) providing an aqueous solution of glyoxylic acid,
b) adjusting the pH of the glyoxylic acid solution to 2.8 to 4 by adding magnesium hydroxide, in case the magnesium-zinc-salt is desired, or by adding aluminum hydroxide, in case the aluminium-zinc-salt or by adding calcium hydroxide or calcium oxide, in case the calcium-zinc-salt is desired,
c) adding zinc dithionite ($ZnS_2O_4$) to the solution obtained in step (b),
d) adjusting the pH of the solution obtained in step (c) to 4.5 to 6.

Preferably, the bases used in step (d) to adjust the pH are in analogy to step (b), i.e. magnesium hydroxide is used for the magnesium-zinc-salt, aluminum hydroxide is used for the aluminium-zinc-salt and calcium hydroxide or calcium oxide is used for the calcium-zinc-salt.

In an embodiment, the pH in step (b) is adjusted to 2.9 to 3.8. In a further embodiment, the pH in step (d) is adjusted to 4.5 to 5.5.

In a further embodiment, the zinc dithionite in step (c) is added in a molar ratio of 1:0.5 to 1:3 (zinc dithionite:glyoxylic acid).

In a further embodiment, the sulfinate salt and the sulfonate salt are isolated by crystallization or precipitation. For this purpose a water-miscible solvent (methanol, ethanol, propanol, isopropanol, acetone, methyl ethyl ketone etc.) may be added to the solution obtained in step (d) to precipitate the salts. The salts can then be separated and dried in a conventional manner, for example by fractionated crystallization from water or a mixture of water and said water-miscible solvents. Drying can be done in a conventional manner, for example by spray drying the solution obtained in step (d) or of the suspension obtained after crystallization.

In a further embodiment, the invention relates to a salt which is obtainable by adjusting the pH of an aqueous solution of glyoxylic acid to 2.8 to 4, preferably 2.9 to 3.8, by reacting it with magnesium hydroxide or aluminum hydroxide or calcium hydroxide, reacting the obtained magnesium or aluminium or calcium salt of glyoxylic acid with zinc dithionite and adjusting the pH to 4.5 to 6, preferably 4.5 to 5.5, and optionally isolating the salt. Isolation of the salt is preferably carried out as described above. In a further embodiment, the zinc dithionite is added in a molar ratio of 1:0.5 to 1:3 (zinc dithionite:glyoxylic acid).

The salts of the invention may be provided in solid form, for example as a powder or granulate, or as an aqueous solution. The solid salts and an aqueous solution thereof are storage stable for a long period of time. Even after storage of the solution for 21 days at a pH of 5 the reducing power of the solution is only very slightly reduced. The water content of the salts of the invention in solid form is, in general, in the range of 0.1 to 3 wt. %, based on dry solids.

For use the salts may be applied in solid form, as an aqueous solution or an aqueous suspension which may be freshly prepared. For example, the aqueous solution or suspension may comprise 10 to 50 wt. % of the compound or composition, based on the total weight of the solution or suspension.

In a further aspect the invention relates to a composition comprising a salt of the invention and conventional additives and auxiliaries such as other metal salts like a metal sulfate.

In an embodiment, the composition of the invention comprises additional reducing agents such as ascorbic acid, isoascorbic acid or salts of these acids, or bisulfites, etc.

The amount of additional reducing agents and/or conventional additives and/or auxiliaries is, in general, less than 30 wt. %, based on the total weight of the composition. Thus, the composition of the invention comprises at least 70 wt. %, in particular at least 80 wt. %, of the salt of the invention, based on the total weight of the solid mixture.

The composition of the invention can be prepared by mixing the components in the desired mixing ratio.

The salts of the invention are reducing agents that are more stable than the corresponding sodium salts and do not develop a sulfur smell and yet have comparable reducing power. The reducing power is, however, higher than that of the corresponding zinc salt. The salts of the invention are thus preferentially used as reducing agents in fields where a high reducing power and high stability over time is required. For example, they can be used as reducing agents in textile printing, in particular in textile discharge printing, in textile bleaching or vat dyeing, or as reducing agents for bleaching minerals, such as kaolin etc., and fibers, for example cellulose fibers. They are preferably used, however, as initiator in emulsion polymerization together with peroxidic initiators in order to allow the polymerization to be carried out at a lower temperature. For this purpose, the salts of the invention may, if desired, be also used together with oxidizable metal ions, such as $Fe^{2+}$, $Mn^{2+}$ etc. Preferably, the salts of the invention are used as reducing agents in the main- and/or post-polymerization of an emulsion polymer in order to reduce the residual monomer content to an acceptable level.

Therefore, the invention also relates to the use of said salts as reducing agents, in particular as reducing agents in textile printing, in particular in textile discharge printing, in textile bleaching or vat dyeing, or as reducing agents for bleaching minerals, such as kaolin etc., and fibers, for example cellulose fibers. Preferably, the invention relates to the use of the salts in emulsion polymerizations. Particularly preferred is the use of the salts in the main- and/or post-polymerization of an emulsion polymer.

The examples below illustrate the invention without limiting it.

SYNTHESIS EXAMPLES

Example 1

Synthesis of a Mixed Magnesium-Zinc-Salt of 2-hydroxy-2-sulfinato/sulfonato acetic acid 59.23 g of a 50 wt % aqueous solution of glyoxylic acid were partially neutralized with 11.67 g $Mg(OH)_2$. For this purpose the glyoxylic acid was charged into a three-necked flask and diluted with 150 ml of water. Subsequently, $Mg(OH)_2$ was added in solid form. The pH has risen to 3.5. The obtained Mg glyoxylate was then reacted with zinc dithionite in a molar ratio of 1:1. The zinc dithionite was added as an aqueous solution (32% in water) via a dropping funnel. The reaction mixture was stirred for 60 min. Additional $Mg(OH)_2$ was slowly added to adapt the pH to 5 and the reaction mixture was stirred for an additional 60 min at room temperature. The reaction mixture was filtered to obtain a colorless clear solution.

The solution was analyzed by iodometric titration. The Mg—Zn— sulfinate/sulfonate solution contained 1.9 wt % magnesium and 5.5 wt % zinc, 7.9 wt % sulfinate, 10.6 wt % sulfonate, and 0.1 wt % sulfite.

The IR spectra in water exhibited peaks at the following wave numbers:

3290 $cm^{-1}$ (74.7% T), 1733 $cm^{-1}$ (47.3% T), 1630 $cm^{-1}$ (75.6% T), 1545 $cm^{-1}$ (75.3% T), 1502 $cm^{-1}$ (83.7% T), 1381 $cm^{-1}$ (81.5% T), 1334 $cm^{-1}$ (81.3% T), 1174 $cm^{-1}$ (61.9% T), 1083 $cm^{-1}$ (78.2% T), 1034 $cm^{-1}$ (76.3% T).

In order to obtain the substance in solid form, the solution can be dried using a lab-scale B-290 Advanced spray dryer from Büchi, Switzerland.

Example 2

Synthesis of a Zinc Salt of 2-hydroxy-2-sulfinato/sulfonato acetic acid 59.23 g of a 50 wt % aqueous solution of glyoxylic acid were partially neutralized with 16.28 g ZnO. For this purpose the glyoxylic acid was charged into a three-necked flask and diluted with 150 ml of water. Subsequently, ZnO was added in solid form. The pH has risen to 3.5. The obtained Zn glyoxylate was then reacted with zinc dithionite in a molar ratio of 1:1. The zinc dithionite was added as an aqueous solution (32% in water) via a dropping funnel. The reaction mixture was stirred for 60 min. Additional ZnO was slowly added to adapt the pH to 5 and the reaction mixture was stirred for an additional 60 min at room temperature. The reaction mixture was filtered to obtain a colorless clear solution.

The solution was analyzed by iodometric titration. The Zn— sulfinate/sulfonate solution contained 11.9 wt % zinc, 8.6 wt % sulfinate, 11.9 wt % sulfonate, and 0.2 wt % sulfite.

The IR spectra in water exhibited peaks at the following wave numbers:

3284 $cm^{-1}$ (75.8% T), 1732 $cm^{-1}$ (47.0% T), 1630 $cm^{-1}$ (76.3% T), 1545 $cm^{-1}$ (75.8% T), 1501 $cm^{-1}$ (83.8% T), 1381 $cm^{-1}$ (82.1% T), 1334 $cm^{-1}$ (81.6% T), 1173 $cm^{-1}$ (62.7% T), 1082 $cm^{-1}$ (78.6% T), 1035 $cm^{-1}$ (78.1% T)

In order to obtain the substance in solid form, the solution can be dried using a lab-scale B-290 Advanced spray dryer from Büchi, Switzerland.

Example 3

Synthesis of a Mixed Aluminium-Zinc-Salt of 2-hydroxy-2-sulfinato/sulfonato acetic acid 59.23 g of a 50 wt % aqueous solution of glyoxylic acid were partially neutralized with 20.80 g $Al(OH)_3$. For this purpose the glyoxylic acid was charged into a three-necked flask and diluted with 150 ml of water. Subsequently, $Al(OH)_3$ was added in solid form. The pH has risen to 3.0. The obtained Al glyoxylate was then reacted with zinc dithionite in a molar ratio of 2:3. The zinc dithionite was added as an aqueous solution (32% in water) via a dropping funnel. The reaction mixture was stirred for 60 min. Additional $Al(OH)_3$ was slowly added to adapt the pH to 4.5 and the reaction mixture was stirred for an additional 60 min at room temperature. The reaction mixture was filtered to obtain a colorless clear solution.

The solution was analyzed by iodometric titration. The obtained Al—Zn— sulfinate/sulfonate solution contained 3.9 wt % sulfinate, 6.2 wt % sulfonate, and 0.1 wt % sulfite.

The values for Zn and Al were determined by X-ray fluorescence spectroscopy using a S2 Ranger device from Bruker under Helium gas: Zn: 2.6 wt %, Al: 0.7 wt %.

The IR spectra in water exhibited peaks at the following wave numbers:

3294 $cm^{-1}$ (47.8% T), 2158 $cm^{-1}$ (94.7% T), 1635 $cm^{-1}$ (63.8% T), 1383 $cm^{-1}$ (85.6% T), 1171 $cm^{-1}$ (81.3% T), 1027 $cm^{-1}$ (78.5% T), 459 $cm^{-1}$ (24.3% T)

In order to obtain the substance in solid form, the solution can be dried using a lab-scale B-290 Advanced spray dryer from Büchi, Switzerland.

Example 4

Stability of the Salt Solutions

The sulfinate content over time of 10 wt % solutions comprising the following salts
a) 2-hydroxy-2-sulfinato acetic acid di sodium salt (47 wt %), 2-hydroxy-2-sulfonato acetic acid di sodium salt (18 wt %), and sodium sulfite (33 wt %),
b) 2-hydroxy-2-sulfinato acetic acid di sodium salt (38 wt %), 2-hydroxy-2-sulfonato acetic acid di sodium salt (57 wt %), sodium sulfite (1 wt %),
c) Zn—Mg— sulfinate, Zn—Mg— sulfonate, and Zn—Mg-sulfite of example 1,
d) Zn— sulfinate, Zn— sulfonate and Zn-sulfite of example 2,
e) Zn—Al— sulfinate, Zn—Al— sulfonate and Zn—Al-sulfite of example 3 was determined by iodometric titration. For comparative purposes the values for solutions a) and b) were also determined at pH 9 which results when dissolving the sodium salts in water. The pH of solutions a) and b) was adjusted to 5 with diluted sulfuric acid. The results are shown in FIG. 1. As can be seen, the Zn—Mg salt and the Zn—Al salt shows improved stability as compared to the corresponding sodium salts. The improved stability is of significant advantage for the user because the solution maintains its reducing power for a longer time so that the solution can be kept and used for a longer time without significant activity loss.

Example 5

Vat Dye Temperature

This method is known from the textile industry and makes use of the reaction of a vat dye (here indanthrene) with reducing agents. The higher the temperature at which a discoloration of the test stick occurs, the more stable is the reducing agent at the test pH. The following vat dye temperatures were determined at pH 5 in 2 wt % solutions in water.

TABELLE 1

| vat dye temperatures at pH = 5 | |
|---|---|
| Reducing agent | vat dye temperature |
| Solution a) | Room temperature |
| Solution b) | Room temperature |
| Solution c) | 72° C. |
| Solution d) | 85° C. |
| Solution e) | 55° C. |

The data confirm the results shown in FIG. 1.

Example 6

Reducing Power

To demonstrate the reducing power of the compounds and compositions of the invention in reducing the residual monomer content in emulsion polymerizations a styrene-n-butylacrylate latex (Liocryl XAS 4727 obtained from Synthopol Chemie GmbH & Co. KG) was used. Styrene and n-butylacrylate monomers were added to the latex to a final content of 5000 ppm each and homogenized. 350 g of the latex were charged into a vessel and the temperature thereof was regulated to 60° C. using a thermostat. The reducing agent and the oxidation agent, tert.-butylhydroperoxide (tBHP), were added simultaneously to the latex at 60° C. in an amount of 0.1 wt. % each, based on the total weight of the latex. The addition rate and the corresponding concentration of the reducing agent mixtures and of the oxidation agent is given in table 2 below. As reducing agent solutions a) to e) given in example 4 were used. The concentration of the sulfinate salts as activity determining substance within the reducing agent mixtures was in each case adjusted to 4 wt %. to ensure comparability.

TABLE 2

| Dosage of oxidation and reducing agent | | |
|---|---|---|
| | Amount of added solution | Addition rate |
| 4 wt % sulfinate solution (10 g in 250 ml H$_2$O) | 8.75 ml (4 × 2.19 ml each) | 0.146 ml/min |
| 2.2 wt % t-BHP solution (5.5 g t-BHP (70 wt %) in 250 ml H$_2$O) | 22.72 ml (4 × 5.68 ml each) | 0.378 ml/min |

Samples were taken from the flask according to the schedule given in table 3:

TABLE 3

| Sample | |
|---|---|
| P0 | Initial, temperature not yet adjusted |
| P1 | Initial, temperature adjusted |
| P2 | Sample after 15 min reaction time |
| P3 | Sample after 30 min reaction time |
| P4 | Sample after 45 min reaction time |
| P5 | Sample after 60 min reaction time |

The residual monomer content was determined as follows:

A Headspace-GC-MS of Perkin Elmer with Headspace-Autosampler and the Multiple Headspace Extraction method were used for determining the residual monomer content. The results for residual n-butylacrylate are shown in table 4 and FIG. 2 and the results for residual styrene are shown in table 5 and FIG. 3.

TABLE 4

| percent decrease of residual n-butylacrylat (BA) content | | | | | | |
|---|---|---|---|---|---|---|
| | | P1 | P2 | P3 | P4 | P5 |
| Solution a) | BA in % | 100 | 64.0 | 34.0 | 21.0 | 11.0 |
| Solution b) | BA in % | 100 | 55.4 | 31.3 | 15.2 | 3.5 |
| Solution c) | BA in % | 100 | 63.2 | 36.1 | 21.0 | 11.3 |
| Solution d) | BA in % | 100 | 67.6 | 52.8 | 34.5 | 20.6 |
| Solution e) | BA in % | 100 | 54.2 | 25.5 | 16.1 | 9.3 |

TABLE 5

| percent decrease of residual styrene (St) content | | | | | | |
|---|---|---|---|---|---|---|
| | | P1 | P2 | P3 | P4 | P5 |
| Solution a) | St in % | 100 | 77.3 | 17.0 | 7.6 | 2.8 |
| Solution b) | St in % | 100 | 45.0 | 17.4 | 3.9 | 0.0 |
| Solution c) | St in % | 100 | 48.9 | 20.7 | 8.3 | 2.9 |
| Solution d) | St in % | 100 | 58.4 | 43.2 | 24.1 | 10.6 |
| Solution e) | St in % | 100 | 43.0 | 6.7 | 7.2 | 2.3 |

Figure 2:
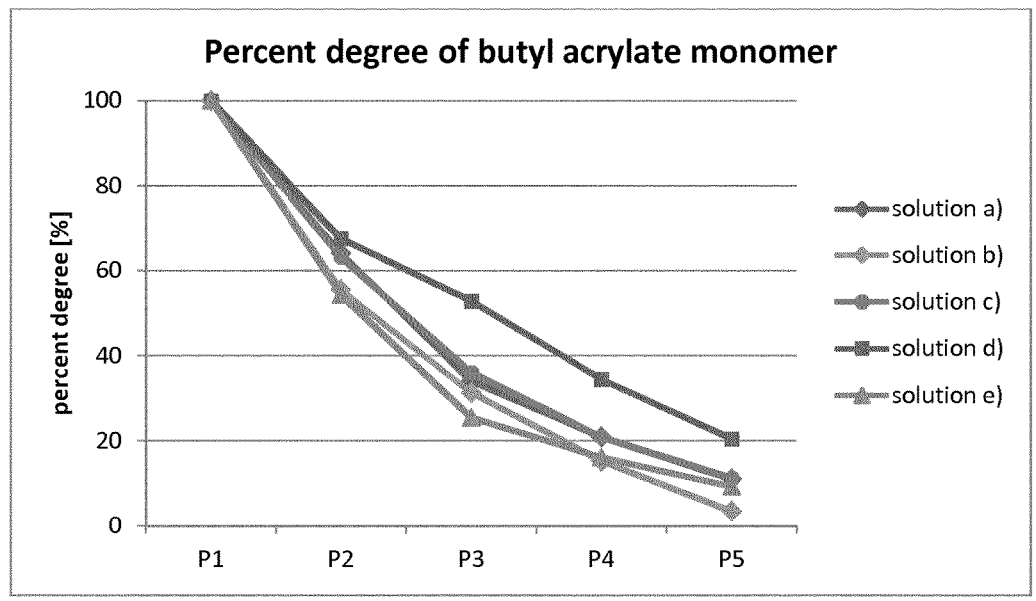
FIG. 2 shows the percent decrease of n-butylacrylate over time in the post-polymerization of a styrene acrylate.
Figure 3:
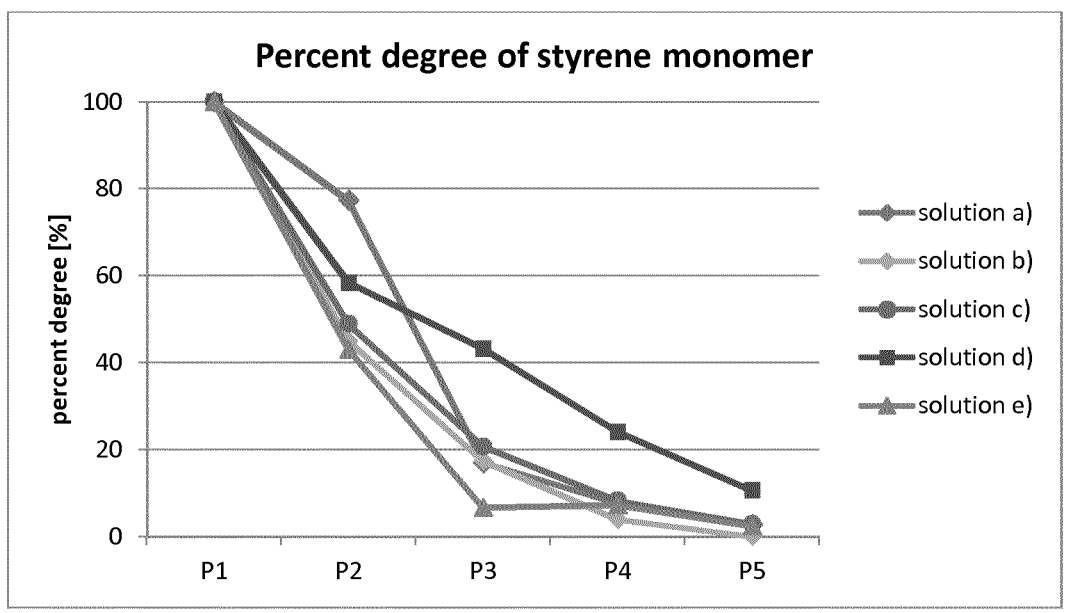
FIG. 3 shows the percent decrease of styrene over time in the post-polymerization of a styrene acrylate.

Tables 4 and 5 and FIGS. 2 and 3 show that the reducing power of solutions c) and e) according to the invention is significantly better than that of solution d).

Example 7

Determination of the Sulfur Smell

The reducing agents were provided as solid and as a 20 wt % solution or suspension. The smell was determined by a panel of 5 test persons and rated in accordance with the classification in table 6. The reducing agents were the salts as given in example 4. The results are given in table 7.

TABLE 6

| Smell classification | |
|---|---|
| Rating | Classification |
| 0 | No sulfur smell |
| 1 | Slight sulfur smell |
| 2 | Significant sulfur smell |
| 3 | Strong sulfur smell |
| 4 | Very strong sulfur smell |

TABELLE 7

| Reducing agent | Classification rating |||||
| --- | --- | --- | --- | --- | --- |
| | Rating |||||
| | 0 | 1 | 2 | 3 | 4 |
| Salt a), solid |  |  | x |  |  |
| Salt a), solution |  |  |  | x |  |
| Salt b), solid |  |  |  | x |  |
| Salt b), solution |  |  |  |  | x |
| Salt d), solid | x |  |  |  |  |
| Salt d), solution | x |  |  |  |  |
| Salt c), solid | x |  |  |  |  |
| Salt c), solution | x |  |  |  |  |
| Salt e), solid | x |  |  |  |  |
| Salt e), solution | x |  |  |  |  |

The salts of the invention do not develop a sulfur smell whereas the sodium salts have at least a significant sulfur smell. This confirms the results given in example 4.

The invention claimed is:

1. A mixed magnesium-zinc-salt or a mixed aluminium-zinc-salt or a mixed calcium-zinc-salt of the sulfinic acid of formula (I)

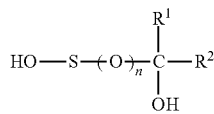

wherein
R$^1$ is H or C$_1$-C$_6$ alkyl,
R$^2$ is COOH, SO$_3$H or CH(OH)S(O)$_n$—OH,
n is 1 and
wherein the acid forms an anion and the counterions are magnesium and zinc ions or aluminium and zinc ions or calcium and zinc ions.

2. The salt of claim 1, wherein R$^1$ is H.
3. The salt of claim 2, wherein R$^2$ is COOH.
4. The salt of claim 1, wherein R$^2$ is COOH.
5. The magnesium-zinc-salt of claim 1, wherein the counterions comprise 40 to 60 mole % magnesium ions and 40 to 60 mole % zinc ions or 45 to 55 mole % magnesium ions and 45 to 55 mole % zinc ions.
6. The salt of claim 5, wherein R$^1$ is H.
7. The salt of claim 5, wherein R$^2$ is COOH.
8. The aluminium-zinc-salt of claim 1, wherein the counterions comprise 25 to 60 mole % aluminium ions and 40 to 75 mole % zinc ions or 30 to 50 mole % aluminium ions and 50 to 70 mole % zinc ions.
9. The salt of claim 8, wherein R$^1$ is H.
10. The salt of claim 8, wherein R$^2$ is COOH.
11. The salt of claim 1, additionally containing a mixed magnesium-zinc-salt or a mixed aluminium-zinc-salt or a mixed calcium-zinc-salt of the sulfonic acid of formula (I')

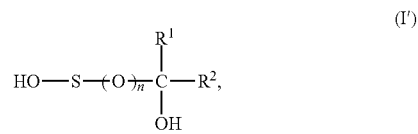

wherein
R$^1$ is H or C$_1$-C$_6$ alkyl,
R$^2$ is COOH, SO$_3$H or CH(OH)S(O)$_n$—OH, and
n is 2.

12. The salt of claim 11, which comprises the sulfinic acid salt and the sulfonic acid salt in a weight ratio of 3:1 to 1:5.
13. The salt of claim 12, which comprises the mixed magnesium-zinc-salt of the sulfinic acid and the mixed magnesium-zinc-salt of the sulfonic acid in a weight ratio of 2:1 to 1:3.
14. The salt of claim 12, which comprises the mixed aluminium-zinc-salt of the sulfinic acid and the mixed aluminium-zinc-salt of the sulfonic acid in a weight ratio of 1:1 to 1:2.
15. The salt of claim 11, which comprises less than 2 wt % of magnesium-zinc-sulfite or aluminium-zinc-sulfite.
16. A salt as defined in claim 11 obtainable by adjusting the pH of an aqueous solution of glyoxylic acid to 3 to 4 by reacting it with magnesium hydroxide or aluminum hydroxide or calcium hydroxide, reacting the obtained magnesium or aluminium or calcium salt of glyoxylic acid with zinc dithionite and adjusting the pH to 4.5 to 6.
17. A method comprising using the salts as defined in claim 1 as a reducing agent.
18. A composition comprising the salt of claim 1 and additional reducing agents and/or auxiliaries.
19. A method comprising using the salts as defined in claim 1 as a reducing agent in emulsion polymerizations.
20. A method comprising using the salts as defined in claim 1 as a reducing agent in a post-polymerization of emulsion polymerizations.

* * * * *